US006194412B1

(12) United States Patent
Ratsimamanga et al.

(10) Patent No.: US 6,194,412 B1
(45) Date of Patent: Feb. 27, 2001

(54) MIXTURES DERIVED FROM GRAINS OF EUGENIA JAMBOLANA LAMARCK PREPARATION AND USE OF SAID MIXTURES AND SOME OF THEIR CONSTITUENTS AS MEDICAMENTS

(75) Inventors: Albert Rakoto Ratsimamanga; Suzanne Rakoto Ratsimamanga; Philippe Rasoanaivo, all of Antananarivo (MG); Jean Leboul, Gometz la Ville (FR); Jean Provost, Monts (FR); Daniel Reisdorf, Thiais (FR)

(73) Assignees: Rhone-Poulenc Rorer S.A., Antony (FR); Institut Malgache de Recherches, Antananarivo (MG)

( * ) Notice: Subject to any disclaimer, the term of this patent is extended or adjusted under 35 U.S.C. 154(b) by 0 days.

(21) Appl. No.: 09/328,421

(22) Filed: Jun. 9, 1999

Related U.S. Application Data

(62) Division of application No. 09/117,843, filed as application No. PCT/FR97/00207 on Feb. 3, 1997, now Pat. No. 5,972,342.

(30) Foreign Application Priority Data

Feb. 6, 1996 (FR) .................................................. 96 01389

(51) Int. Cl.[7] .......................... A61K 31/50; A01N 43/60; A01N 31/495; C07D 241/00
(52) U.S. Cl. .................................. 514/252.1; 424/195.1; 514/183; 544/336
(58) Field of Search ................ 514/252.1, 183; 544/336, 358; 424/195.1

(56) References Cited

U.S. PATENT DOCUMENTS 3,660,571   5/1972   Kodama et al. .

FOREIGN PATENT DOCUMENTS 2 159 923   6/1973   (DE) .
2 465 484   3/1981   (FR) .

OTHER PUBLICATIONS

Whitmann et al Z.Lebensm.–Unters Forsch (1989) 188 (3) 212–20 CAPLUS 1989:455721.*
Tsuchida et al Nippon Shokuhin Kogyo Gakkaishi 37(2), 154–61, 1990 CA113:229877 (1990).*
Tsuchida et al Dev Food Sci 13, 85–94 1986 CA 105:170812 (1986).*
Tsuchida et al Biol. Chem 40(5) 921–925 (1976) CA85:45165 (1976).*
Tsuchida et al Biol. Chem 39(5) 1143–1148 (1975) CA84:17618 (1975).*
Forlano et al An Asoc Quim Argent 60 (3/4) 323–30 (1972) CAPLUS 1973:4457.*
Bashiardes et al CA 130:153670 WO9903840 Jan. 28, 1990.*
Derwent Abstract of FR 2 465 484, Mar. 27, 1981.
Derwent Abstract of DE 2 159 923, Jun. 16, 1973.
Derwent Abstract of FR 6114 M, Jun. 17, 1968.
Kitaoka et al., "2,5–Bis–D–Glucopyrazine," Chemical Abstracts, 74(25):142298e (1971).

* cited by examiner

*Primary Examiner*—Herbert J. Lilling
(74) *Attorney, Agent, or Firm*—Finnegan, Henderson, Farabow, Garrett, & Dunner L.L.P.

(57) ABSTRACT

The present invention relates to mixtures which can be isolated from grains of Eugenis Jambolana Lamarck, the preparation of such mixtures, the medicaments containing said mixtures or constituents of said mixtures, and the use of these mixtures and constituents for the preparation of a medicament.

2 Claims, No Drawings

MIXTURES DERIVED FROM GRAINS OF EUGENIA JAMBOLANA LAMARCK PREPARATION AND USE OF SAID MIXTURES AND SOME OF THEIR CONSTITUENTS AS MEDICAMENTS

This is a division of application Ser. No. 09/117,843, filed Aug. 6. 1998, now U.S. Pat. No. 5,972,342 which is a national stage of International Application No. PCT/FR97/00207, filed Feb. 3, 1997 all of which are incorporated herein by reference.

The present invention relates to mixtures which can be isolated from Eugenia Jambolana Lamarck seeds (Myrtaceae family), medicaments containing these mixtures or some of their constituents, the use of these mixtures and constituents for the preparation of an antidiabetic medicament and their preparations.

A plant extract prepared from Eugenia Jambolana seeds or bark containing a polyphenol and sterol mixed complex is described in patent FR 2,465,484.

New mixtures which can be isolated from Eugenia Jambolana Lamarck seeds, and which are free of polyphenol and sterol complex, as well as certain constituents of these mixtures endowed with hypoglycaemic properties, have now been found.

These mixtures are characterized in that they are free of polyphenol and sterol derivatives and can be isolated by grinding Eugenia Jambolana Lamarck seeds, maceration of the powder with a lower aliphatic alcohol with the use of heat, filtration, recovery of the insoluble part no longer containing polyphenol and sterol compounds, treatment of the insoluble part with an ammoniacal solution, treatment of the ammoniacal mixture with a lower aliphatic alcohol with the use of heat, filtration, recovery of the insoluble matter and drying this insoluble matter which constitutes the mixture I, then optionally treatment of the mixture I with a water-lower aliphatic alcohol solution, filtration, partial concentration of the filtrate, purification on nonpolar adsorbent resins, partial concentration, centrifugation, ultrafiltration and isolation of the mixture II.

From the mixture II, there may also be separated sodium oxamate and the compounds of formula:

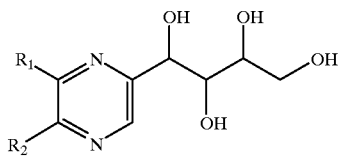
(I)

in which either $R_1$ represents a hydrogen atom and $R_2$ represents a chain of formula:

$$—CH_2—CHOH—CHOH—CH_2OH \qquad (A)$$

$$—CHOH—CHOH—CHOH—CH_2OH \qquad (B)$$

or $R_1$ represents a chain of formula (A) and $R_2$ represents a hydrogen atom.

Sodium oxamate has already been described by TOUSSAINT, Ann., 120, 237 (1861).

The compounds of formula (I) have already been described by KUHN et al., Ann., 644, 122–127 (1961); TSUCHIDA et al., Agr. Biol. Chem., 39 (5), 1143–1148 (1975); TSUCHIDA et al., Agr. Biol. Chem., 40 (5), 921–925 (1976); TSUCHIDA et al., Nippon Shokuhin Kogyo Gakkaishi, 37, 154–161 (1990) and AVALOS et al., tetrahedron, 49, 2655–2675 (1993).

The present invention also relates to the process for preparing the mixture I from dried and finely ground Eugenia Jambolana Lamarck seeds.

The powder is screened, preferably with the aid of a normalized screen with holes 0.5 μm in diameter and then subjected to the following treatment:

a—maceration, with stirring, in a lower aliphatic alcohol, at a temperature of between 40 and 70° C., b—filtration under vacuum and recovery of the insoluble matter, c—maceration, with stirring, of the insoluble matter with a lower aliphatic alcohol at a temperature of between 40 and 70° C., d—filtration under vacuum and removal of the alcoholic phases containing mainly the undesirable polyphenols and sterols, e—taking up the insoluble matter in an anmmoniacal solution at a temperature of between 10 and 30° C., f—taking up the whole wet ammoniacal mass in a water-lower aliphatic alcohol solution, at a temperature of between 40 and 70° C., g—filtration and removal of the alcoholic solution, h—washing of the insoluble matter with a lower aliphatic alcohol, filtration and removal of the alcoholic solution, i—recovery of the insoluble matter and drying.

In step a, the procedure is generally carried out by means of 2 to 10 liters of a lower aliphatic alcohol such as methanol or ethanol per 1 kg of screened powder. Preferably, 5 liters of ethanol with a titre of 93–95° Gay Lussac are used at 60° C. for 1 hour.

The filtration of step b is preferably carried out under a vacuum of 40 kPa.

In step c, the procedure is generally carried out by means of 2 to 10 liters of a lower aliphatic alcohol such as methanol or ethanol per 1 kg of starting screened powder. Preferably, 4 liters of ethanol with a titre of 93–95° Gay Lussac are used at a temperature of 60° C. for 1 hour.

The filtration of step d is preferably carried out under a vacuum of 40 kPa.

In step e, per 1 kg of starting screened powder, 750 to 1250 ml of an aqueous ammoniacal solution preferably containing 350 ml of 28% ammonium hydroxide per 1000 ml are generally used. It is particularly advantageous to use 1 liter of the aqueous ammoniacal solution and to carry out the procedure for 10 to 30 hours and, preferably, 20 hours at a temperature close to 20° C.

In step f, the wet ammoniacal mass obtained from 1 kg of starting screened powder is generally taken up, with stirring, in 2 to 10 liters of a lower aliphatic alcohol-water mixture (methanol or ethanol for example) (70/30 to 80/20 by volume) and, preferably, in 5 liters of an ethanol-water mixture (75/25 by volume), at 60° C., for 1 hour.

In step g, the filtration is preferably carried out on a cotton cloth and under a vacuum of about 80 kPa.

In step h, the washing is generally carried out with 500 to 1500 ml of a lower aliphatic alcohol (methanol or ethanol for example) per 1 kg of starting screened powder and, preferably, with 1 liter of ethanol and the filtration is carried out on a cotton cloth and under a vacuum of about 80 kPa.

In step i, the drying is preferably carried out in the open air and protected from light.

The present invention also relates to the process for preparing the mixture II.

The mixture I obtained above is subjected to the following operations:

j—treatment of the mixture I by means of a water-lower aliphatic alcohol solution, k—decantation and then, on the one hand, drawing off the top phase which is filtered to give the filtrate 1 and, on the other hand, treating the bottom phase with water and filtration to give the filtrate 2, pooling of the filtrates 1 and 2 and concentration to aqueous phase, l—treatment with a nonpolar adsorbent resin and then filtration, m—concentration of the filtrate, filtration and then ultrafiltration, n—freeze-drying and isolation of the extract II.

In step j, 10 to 25 liters of the water-lower aliphatic alcohol solution (methanol or ethanol for example) (95/5 to 90/10 by volume) are generally used per 1 kg of the mixture I. It is preferable to carry out the procedure in 18 liters of a water-ethanol solution (17.7–0.93 by volume).

In step k, it is preferable to filter the top phase on a cotton cloth. It is advantageous to add, per 1 kg of the mixture I, 10 to 25 liters of water to the bottom phase and in particular 10 liters and to filter on sintered glass.

In step k, the concentration is generally carried out in a thermosiphon concentrator at a temperature of 35° C. under a vacuum of 0.4 kPa.

In step l, S861 resin or XAD-type resins marketed by Rhom and Hass are preferably used and the mixture is filtered on sintered glass.

In step m, the concentration is generally carried out in a thermosiphon concentrator at a temperature of 35° C. under a vacuum of 0.4 kPa. It is also advantageous to carry out 3 successive ultrafiltrations on 10 kd, 3 kd and 1 kd cartridges.

The present invention also relates to the process for preparing sodium oxamate and the compounds of formula (I).

The said process consists in subjecting the mixture II to the following operations:

o—chromatography of the mixture II on an infusorial earth column, recovery of the fractions containing the 4 products and pooling of these fractions into a single fraction, p—chromatography of the fraction previously obtained on a Sephadex® column in order to obtain sodium oxamate, the compound of formula (I) for which $R_1$ represents a hydrogen atom and $R_2$ represents a residue (B) and a mixture of the compound of formula (I) for which $R_1$ represents a hydrogen atom and $R_2$ represents a residue (A) and of the compound of formula (I) for which $R_1$ represents a residue (A) and $R_2$ represents a hydrogen atom, q—optionally, chromatography of the mixture of the compound of formula (I) for which $R_1$ represents a hydrogen atom and $R_2$ represents a residue (A) and of the compound of formula (I) for which $R_1$ represents a residue (B) and $R_2$ represents a hydrogen atom by HPLC.

The chromatography of step o is carried out by means of an organic solvent such as heptane, ethyl acetate or a lower aliphatic alcohol. Preferably, a CHEM ELUDT® column marketed by Prolabo is used, saturated with water and then eluted successively with heptane, a heptane-ethyl acetate mixture (50/50 by volume), ethyl acetate, an ethyl acetate-n-butanol mixture (95/5; 90/10; 80/20; 50/50; 20/80), n-butanol, and an n-butanol-water mixture (98/2 and then 95/5 by volume).

The chromatography of step p is preferably carried out by means of a water-ethanol mixture (50/50 by volume).

The chromatography of step q is generally carried out on a YMC 180DS-AQ column marketed by AIT with, as eluent, a water containing 0.1% of formic acid mixture.

In the preceding definitions and those which follow, the lower aliphatic alcohols preferably contain 1 to 4 carbon atoms.

The medicaments containing the mixtures I or II or sodium oxamate or one or more compounds of formula (I) generally form part of the invention.

The present invention also relates to the use of the mixtures I and II, of sodium oxamate and of the compounds of formula (I) or a mixture of these with the preparation of medicaments for the treatment or prevention of diabetes and of the complications of diabetes.

The following examples illustrate the invention.

EXAMPLE 1

Preparation of the Mixture I

Eugenia Jambolana Lamarck seeds are dried in the open air, protected from light, and then finely ground. The powder thus obtained is screened with the aid of a screen of mesh 0.5 $\mu$m. 1 kg of screened powder is macerated, with mechanical stirring, in 5 liters of ethanol with a titre of 93–95° Gay Lussac, for one hour at 60° C. After filtration under vacuum, the insoluble matter is further treated under the same conditions with 4 liters of ethanol of the same titre at 60° C. for a further one hour. The two ethanolic extracts containing mainly the undesirable polyphenol and sterol complex are removed. After complete filtration, the insoluble matter is taken up in 1 liter of ammoniacal solution (28% $NH_4OH$ 350 ml and distilled $H_2O$ in sufficient quantity to obtain 1 liter of solution) and the mixture is left in contact for about 20 hours at a temperature close to 20° C. The wet ammoniacal mass is allowed to macerate again in 5 liters of the ethanol of titre 93 to 95° Gay Lussac-water mixture (75/25 by volume), with mechanical stirring, for 1 hour at 60° C. The insoluble matter is filtered and it is washed with 1 liter of ethanol of the same titre; the filtrate and the washings are removed. The final insoluble matter is dried in the open air and protected from light. The mixture I is thus obtained in the form of a powder which is free of polyphenol and sterol derivatives. The yield from the pulverized and screened seeds is 80%.

EXAMPLE 2

Preparation of the Mixture II 1 kg of the mixture I obtained in Example 1, in a solution containing 17.7 liters of water and 0.93 liter of ethanol, is stirred for 3 hours. After decantation overnight, on the one hand, the top phase (13.5 liters) is drawn off and then filtered on a cotton cloth in a 7-liter filter (Schott) to give the filtrate 1 (13.5 liters) and, on the other hand, the bottom phase is stirred for 1 hour with 20 liters of water, filtered on No. 3 sintered glass to give the filtrate 2 (24 liters). The filtrates 1 and 2 are pooled and then concentrated in aqueous phase (33.5 liters) in a thermosiphon concentrator (Schott) at 35° C. under a vacuum of 0.4 kPa. The concentrate is stirred for one hour with 2.5 liters of S861 resin (Rhom and Haas) and then filtered on No. 3 sintered glass. The filtrate is concentrated in a thermosiphon concentrator (Schott) at 35° C. and then under a vacuum of 0.4 kPa to 5.5 liters. The concentrate is centrifuged in a tubular centrifuge (centrifugal force 62000 g) and filtered on a 0.22 $\mu$m filter (Gelman suporcap 100 type) pump. After 3 successive ultrafiltrations on 10 Kd, 3 Kd and 1 Kd cartridges and freeze-drying, 25 g of the mixture II are obtained in the form of a dark brown hygroscopic powder.

EXAMPLE 3
Constituents Obtained from the Mixture II 525 mg of the mixture II obtained in Example 2 in solution in 1.1 ml of milli Q-filtered water are chromatographed on a CHEM ELUT® column marketed by PROLABO, 50 cm in height and with a diameter of 1 cm, saturated with milli Q-filtered water. The elution is carried out with heptane using increasing gradients of ethyl acetate and then of n-butanol, of n-butanol/hydrochloric acid and of water (fraction 1: heptane; fraction 2: heptane/ethyl acetate (50/50 by volume); fractions 3–4: ethyl acetate; fractions 5–6: ethyl acetate/n-butanol (95/5 by volume), fractions 7–8: ethyl acetate/n-butanol (90/10 by volume), fractions 9–10: ethyl acetate/n-butanol (80/20 by volume); fractions 11–12: ethyl acetate/n-butanol (50/50 by volume), fractions 13–14: ethyl acetate/n-butanol (20/80 by volume), fractions 15–16: n-butanol, fractions 17–18: n-butanol/water (98/2 by volume), fractions 19–21: n-butanol/water (95/5 by volume). 50 ml fractions are collected. Fractions 19 to 21 are combined and concentrated to dryness under reduced pressure. 108 mg of a fraction is thus obtained which is chromatographed on a Sephadex® LH20 column marketed by Pharmacia (height 100 cm, diameter 1 cm) produced with a methanol-water mixture (50—50 by volume). The elution is carried out with the same eluent mixture; 1 ml fractions are collected.

1—Fractions 88 to 91 are combined and concentrated to dryness. 14.4 mg of a product are obtained, which product gives, upon crystallization from 0.5 ml of ethanol, 2 mg of 2,5-di-(tetrahydroxybutyl)pyrazine in the form of white crystals whose characteristics are the following:

optical rotation $[\alpha]^{20}$ (Na 589)=−137°±2.0 (dimethyl sulphoxide; c=0.5), infrared spectrum produced on a Nicolet 60SX-R apparatus in solution in KBr, main characteristic absorption bands: 3281 $cm^{-1}$ ($\nu$ bound OH groups including $H_2O$), 2972+2940+2901+2880 $cm^{-1}$ ($\nu$ CH of the $CH_2$ and CHOH groups), 2733 $cm^{-1}$ ($\nu$ bound OH groups), 1635 $cm^{-1}$ (deformations of the OH groups, including $H_2O$), 1491 $cm^{-1}$ ($\nu$ C=C and C=N of the pyrazine nucleus), 1449 $cm^{-1}$ ($\nu$ C=C and C=N of the pyrazine nucleus+ deformations of the OH groups), 1413 $cm^{-1}$ (deformations of the OH groups), 1343 $cm^{-1}$ ($\nu$ C=C and C=N of the pyrazine nucleus), 1309+1290+1251+1215+1181+1161+1123 $cm^{-1}$ (deformations of the CH groups), 1092 $cm^{-1}$ ($\nu$ CO of the secondary alcohols), 1048+1035 $cm^{-1}$ ($\nu$ CO of the primary alcohols+ pyrazine nucleus), 947+899+854 $cm^{-1}$ (secondary alcohols), 877 $cm^{-1}$ ($\nu$ CH of the pyrazine nucleus), 727 $cm^{-1}$ (pyrazine nucleus+deformations of the OH groups), 639 $cm^{-1}$ (pyrazine nucleus), 607+531 $cm^{-1}$ broad (deformations of the OH groups), 451+411 $cm^{-1}$ (pyrazine nucleus), mass spectrum performed on a FINNIGAN TSQ46 apparatus, mass ionization mode M/z=321 (ME)+, $^1$H NMR spectrum (600 MHz, DMSO, chemical shift in ppm): 3.40 and 3.61 (2 mts, 2H each: $CH_2$ at position 4', 4"); 3.58 (2 mts, 2H each: CH at position 2', 2", 3', 3"); 4.36 (broad t, 2H: OH at position 4', 4"); 4.40 (d, J=7.2 Hz, 2H: OH at position 2', 2"); 4.63 (d, J=4.8 Hz, 2H: OH at position 3', 3"); 4.95 (dd J=6.0 and 0.6 Hz, 2H: CH at position 1', 1"); 5.30 (d, J=6.0 Hz, 2H: OH at position 1', 1"); 8.61 (s, 2H, CH at position 3 and 6), ultraviolet spectrum: $\lambda$max=275 nm ($\epsilon$=8260); 206 nm ($\epsilon$=10220) (c=19 mg/ml; water), $\epsilon$max=276 nm ($\epsilon$=7960); 206 nm ($\epsilon$=9920) (c=19 mg/ml; HCl 0.1N), $\epsilon$max=275 nm ($\epsilon$=7690); (c=19 mg/ml; KOH 0.1N), HPLC on Y.M.C. 180DS-AQ column of 150×4.6 mm (batch AIT/DE940377) marketed by AIT, isocratic elution $H_2O$ +0.1% formic acid with a flow rate of 1 ml/min, UV detection at 270 nm, retention time: 2 min 32 s.

2—Fractions 92 and 93 are combined and concentrated to dryness. 9 mg of a fraction are obtained, which fraction gives, upon crystallization from 0.5 ml of ethanol, 1.2 mg of sodium oxamate having the same characteristics as those described by TOUSSAINT, Ann., 120, 237 (1861).

3—Fractions 94 to 97 are combined and concentrated to dryness. 25.9 mg of a fraction are obtained, which fraction gives, upon crystallization from 0.5 ml of ethanol, 6.2 mg of a mixture of 2-(tetrahydroxybutyl)-5-(2',3',4'-trihydroxybutyl)pyrazine and 2-(tetrahydroxybutyl)-6-(2',3',4'-trihydroxybutyl)pyrazine which is further separated by HPLC on a Y.M.C. 180DS-AQ column of 150×4.6 mm (batch AIT/DE940377); isocratic elution $H_2O$ +0.1% formic acid with a flow rate of 1 ml/min, UV detection at 270 nm.

5.2 mg of 2-(tetrahydroxybutyl)-5-(2',3',4'-trihydroxybutyl)pyrazine are thus obtained, which has the following characteristics:

optical rotation $[\alpha]^2$ (Na 589)=−116.3°±1.7 (dimethyl sulphoxide; c=0.5), infrared spectrum performed on a Nicolet 60SX-R apparatus in solution in KBr, main characteristic absorption bands at 3398 $cm^{-1}$ ($\nu$ bound OH groups including $H_2O$), 2951+2922+2891 $cm^{-1}$ ($\nu$ CH of the CHOH groups), 2761 $cm^{-1}$ ($\nu$ bound OH groups), 1636 $cm^{-1}$ (deformations of the OH groups, including $H_2O$), 1483+1463 $cm^{-1}$ ($\nu$C=C and C=N of the pyrazine nucleus), 1411 $cm^{-1}$ (deformation of the OH groups), 1367+1328+1270+1227+1191 $cm^{-1}$ (deformation of the CH groups), 1071 $cm^{-1}$ ($\nu$ CO of the secondary alcohols), 1041 $cm^{-1}$ ($\nu$ CO of the primary alcohols+ pyrazine nucleus), 943+897 $cm^1$ (secondary alcohols), 869 $cm^{-1}$ ($\nu$ CH of the pyrazine nucleus), 645 $cm^{-1}$ (CH of the pyrazine nucleus), 607 $cm^{-1}$ broad (deformations of the OH groups), 446+409 $cm^{-1}$ (pyrazine nucleus), mass spectrum performed on a FINNIGAN TSQ46 apparatus, mass ionization mode M/z=305 (MH)+, $^1$H NMR spectrum (600 MHz, DMSO, chemical shift in ppm): 2.70 and 3.04 (2 dd, J=9.0 and 15.0 Hz and J=3.0 and 15.0 Hz, 1H each: $CH_2$ at position 1"); between 3.30 and 3.45 (mts, CH at position 3", 4', 4"); between 3.53 and 3.65 (mts, 4H: CH at position 2', 3', 4', 4"), 3.73 (mt, 1H: CH at position 2"); 4.37 (broad t, 1H: OH at position 4'); 4.42 (mt, 2H: OH at position 2' and 4"); 4.60 (d, J=6 Hz, 1H: OH at position 2"); 4.63 (d, J=6 Hz, 1H: OH at 3'); 4.67 (d, J=6 Hz, 1H: OH at position 3"); 4.92 (dd J=6.0 and 0.6 Hz, 1H: CH at position 1'); 5.30 (d, J=6.0 Hz, 1H : OH at position 1'); 8.39 (s, 1H: CH at position 6); 8.61 (s, 1H: CH at position 3), ultraviolet spectrum: $\lambda$max=276 nm ($\epsilon$=7756); 206 nm ($\epsilon$=8738) (c=19 mg/ml; water), $\lambda$max=277 nm ($\epsilon$=7218); 208 nm ($\epsilon$=7171) (c=19 mg/ml; HCl 0.1 N), $\lambda$max=276 nm ($\epsilon$=7467) (c=19 mg/ml; KOH 0.1N), HPLC on Y.M.C. 180DS-AQ column of 150×4.6 mm (batch AIT/DE940377) marketed by AIT, isocratic elution $H_2O$ +0.1% formic acid with a flow rate of 1 ml/min, UV detection at 270 nm, retention time: 3 min 75 s and 1 mg of 2-(tetrahydroxybutyl)-6-(2',3',4'-trihydroxybutyl)pyrazine which has the following characteristics:

$^1$H NMR spectrum (600 MHz, DMSO, chemical shift in ppm): 2.70 and 3.04 (2 dd, J=9.0 and 15.0 Hz and J=3.0 and 15.0 Hz, 1H each: $CH_2$ at position 1"); between 3.30 and 3.45 (mts, CH at position 3", 4', 4"); between 3.53 and 3.65 (mts, 4H: CH at position 2', 3', 4', 4"), 3.73 (mt, 1H: CH at position 2"); 4.37 (broad t, 1H: OH at position 4'); 4.42 (mt, 2H: OH at position 2'and 4"); 4.60 (d, J=6 Hz, 1H: OH at position 2"); 4.63 (d, J=6 Hz, 1H: OH at 3'); 4.67 (d, J=6 Hz, 1H: OH at position 3"); 4.92 (dd J=6.0 and 0.6 Hz, 1H: CH at position 1'); 5.30 (d, J=6.0 Hz: 1H, OH at position 1'); 8.31 (s, 1H: CH at position 5); 8.53 (s, 1H: CH at position 3), HPLC on Y.M.C. 180DS-AQ column of 150×4.6 mm (batch AIT/DE940377) marketed by AIT, isocratic elution $H_2O$ +0.1% formic acid with a flow rate of 1 ml/min, UV detection at 270 nm, retention time: 3 min 61 s.

The hypoglycaemic activity of the mixtures I and II, of sodium oxamate and of the compounds of formula (I) have been determined in mice made diabetic with streptozocin and in normal mice with post-prandial hyperglycaemia according to the following procedures:

I—Mice made Diabetic with Streptozotocin

Swiss albino mice weighing between 22 and 25 g are made diabetic with streptozotocin administered by intraperitoneal injection at a dose of 210 or 265 mg/Kg of mouse, diluted in a citrate buffer at a concentration such that each mouse receives 0.2 ml of the solution on day 1 (D1). 3 to 4 days later, a check is made on 2 to 3 mice to see if the diabetes is established (glycaemia greater than 7.2 mmol/liter (130 mg per 100 ml). The glycaemia is then measured after starving for 4 hours. If the mice have become diabetic, they are divided into batches of 5 to 7 mice. Each of the batches receives, from D1 and daily, a selected dose of product. The administration is made once a day and at a fixed time, by gastric intubation and in a volume of 0.4 ml of distilled water as vehicle. Two batches of controls are made up:

one batch of untreated diabetic mice one batch or normal mice

These two batches of controls receive 0.4 ml of vehicle by gastric intubation and simultaneously with the treated mice.

The treatment lasts for 4 days. On the 5th day (D5), there is no administration of product. After fasting for 4 hours, the final glycaemias are measured.

II—Normal Mice with Post-prandial Hyperglycaemia

Swiss albino mice weighing between 22 and 25 g are made to have post-prandial hyperglycaemia by the following procedure:

fasting 2 hours food in excess for 1 hour fasting 2 hours

The glycaemia is measured at the end of the last two hours of fasting, which constitutes the glycaemia at time T0. The mice are then divided into homogeneous batches according to the measured glycaemias. The products to be evaluated are administered without delay by gastric intubation in 0.4 ml of distilled water. The control batch receives the excipient (0.4 ml of distilled water). After one hour, the final glycaemias are measured which constitute the glycaemia at time T60.

Results obtained on the glycaemia of mice made diabetic with streptozotocin

| PRODUCTS mg/mouse/day | NUMBER OF MICE | GLYCAEMIA AT D1 mg/100 ml | GLYCAEMIA AT D5 mg/100 ml | % inhibition |
|---|---|---|---|---|
| Sodium oxamate (0.5 mg) | 5 | 153.40 ± 11.53 | 89.90 ± 13.94 | −41.46 |
| Mixture II (0.5 mg) | 5 | 270.50 ± 58.72 | 117.50 ± 17.35 | −56.56 |
| 2-(tetrahydroxybutyl)-5-(2',3',4'-trihydroxybutyl)-pyrazine (0.5 mg) | 5 | 304.25 ± 99.35 | 164.50 ± 95.13 | −45.93 |
| 2-(tetrahydroxybutyl)-5-(2',3',4'-trihydroxybutyl)-pyrazine and 2-(tetrahydroxybutyl)-6-(2',3',4'-trihydroxybutyl)pyrazine (50/50) (0.25 mg) | 6 | 320.83 ± 130.30 | 174.00 ± 97.74 | −45.77 |
| Controls | 5 | 221.66 ± 50.17 | 210.33 ± 20.07 | −5.11 |

Results obtained on the glycaemia of normal mice with post-prandial hyperglycaemia

| PRODUCTS mg/mouse/day | NUMBER OF MICE | GLYCAEMIA AT T0 mg/100 ml | GLYCAEMIA AT T60 mg/100 ml | % inhibition |
|---|---|---|---|---|
| Mixture I (5 mg) | 5 | 129.50 ± 29.06 | 87.60 ± 14.16 | −32.35 |
| Sodium oxamate (0.5 mg) | 15 | 136.46 ± 23.69 | 102.93 ± 20.95 | −24.57 |
| Mixture II (0.5 mg) | 15 | 133.93 ± 17.50 | 105.60 ± 16.91 | −21.15 |
| 2,5-di(tetrahydroxybutyl) pyrazine (0.5 mg) butyl)pyrazine (0.5 mg) | 10 | 136.25 ± 16.92 | 102.41 ± 14.12 | −24.83 |
| 2-(tetrahydroxybutyl)-5-(2',3',4'-trihydroxybutyl)pyrazine (0.5 mg) | 10 | 128.75 ± 21.23 | 90.50 ± 19.55 | −29.70 |
| 2-(tetrahydroxybutyl)-5-(2',3',4'-trihydroxybutyl)pyrazine and 2-(tetrahydroxybutyl)-6-(2',3',4'-trihydroxybutyl)pyrazine (50/50) (0.25 mg) | 5 | 126.60 ± 17.03 | 100.60 ± 16.88 | −20.53 |
| Controls | 10 | 137.83 ± 13.99 | 130.50 ± 20.23 | −5.32 |

The mixtures according to the invention, the sodium oxamate and the compounds of formula (I) have a low toxicity. Their $LD_{50}$ is greater than 2000 mg/kg orally in mice.

The mixtures according to the invention, the sodium oxamate and the compounds of formula (I) reduce the glycaemia in a diabetic subject and are therefore useful in the treatment of diabetes and the complications of diabetes.

When these products are used in monotherapy in the treatment of diabetes, there is no risk of hypoglycaemia. They are true antidiabetic agents. It appears that this effect results from a peripheral increase in glucose. The products do not significantly stimulate the secretion of insulin but the presence of small quantities of insulin is necessary for their action.

In sand rats (Psammomys obesus) which are spontaneously diabetic in captivity, the products decrease hyperglycaemia, prevent or decrease cataract and restore a degree of fertility.

In human therapy, these products are therefore useful in the prevention and treatment of diabetes and especially type II diabetes (NID diabetes) not exhibiting acetonuria, obese diabetes, diabetes at the age of about fifty, metaplethoric diabetes, diabetes affecting the elderly and mild diabetes. They can be used as a supplement to insulin therapy (because of their insulin-potentiating activity) in insulin-dependent diabetes where they make it possible to gradually reduce the dose of insulin, unstable diabetes, insulin-resistant diabetes, and as a supplement to hypoglycaemic sulphamides when these do not provide a sufficient decrease in glycaemia. These products can also be used in the complications of diabetes such as hyperlipaemias, lipid metabolism disorders, dyslipaemias and obesity. They are also useful in the prevention and treatment of the lesions of atherosclerosis and their complications (coronopathies, myocardial infarction, cardiomyopathies, progression of these three complications into left ventricular insufficiency, various arteriopathies, arteritis of the lower limbs with claudication and progression into ulcers and gangrene, cerebral vascular insufficiency and its complications and sexual impotence of vascular origin), diabetic retinopathy and all its manifestations (increase in capillary permeability, dilation and capillary thrombosis, microaneurysms, arteriovenous shunt, venous dilation, punctiform and macular haemorrhages, exudates, macular oedemas, manifestations of proliferative retinopathy: neovessels, proliferative retinitis scars, haemorrhages of the vitreous body, retinal detachment), diabetic cataract, diabetic neuropathy in its various forms (peripheral polyneuropathies and its manifestations such as paresthesias, hyperesthesias and pain, mononeuropathies, radiculopathies, autonomous neuropathies, diabetic amyotrophies), the manifestations of diabetic foot (ulcers of the lower extremities and of the foot), diabetic nephropathy in its two diffuse and nodular forms, atheromatoses (rise in HDL lipoproteins promoting the elimination of cholesterol from the atheroma plaques, decrease in the LDL lipoproteins, decrease in the LDL/HDL ratio, inhibition of oxidation of the LDLs, decrease in platelet adhesiveness), hyperlipaemias and dyslipaemias (hypercholesterolaemias, hypertriglyceridaemias, normalization of the fatty acid level, normalization of the uricaemia, normalization of the A and B apoproteins), cataracts, high blood pressure and its consequences.

The medicaments according to the invention consist of a mixture according to the invention, sodium oxamate, a compound of formula (I) or a combination of these products, in the pure state or in the form of a composition in which it is combined with any other pharmaceutically compatible product which may be inert or physiologically active. The medicaments according to the invention can be used orally, parenterally, rectally or topically.

As solid compositions for oral administration, there may be used tablets, pills, powders (gelatine capsules, cachets) or granules. In these compositions, the active ingredient according to the invention is mixed with one or more inert diluents, such as starch, cellulose, sucrose, lactose or silica, under an argon stream. These compositions may also comprise substances other than the diluents, for example one or more lubricants such as magnesium stearate or talc, a colorant, a coating (sugar-coated tablets) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than the diluents, for example wetting, sweetening, thickening, flavouring or stabilizing products.

The sterile compositions for parenteral administration may preferably be solutions in aqueous or nonaqueous form, suspensions or emulsions. As solvent or vehicle, there may be used water, propylene glycol, polyethylene glycol, vegetable oils, in particular olive oil, injectable organic esters, for example ethyl oleate or other suitable organic solvents. These compositions may also contain adjuvants, in particular wetting, isotonizing, emulsifying, dispersing and stabilizing agents. Sterilization can be performed in several ways, for example by aseptizing filtration, by incorporating sterilizing agents into the composition, by irradiation or by heating. They can also be prepared in the form of sterile solid compositions which can be dissolved at the time of use in sterile water or any other injectable sterile medium.

The compositions for rectal administration are suppositories or rectal capsules which contain, in addition to the active product, excipients such as cocoa butter, semisynthetic glycerides or polyethylene glycols.

The compositions for topical administration may be for example creams, lotions, collyria, collutoria, nasal drops or aerosols.

The doses depend on the desired effect, the duration of treatment and the route of administration used; they are generally between 150 mg and 600 mg per day via the oral route for an adult with unit doses ranging from 50 mg to 200 mg of active substance.

In general, the doctor will determine the appropriate dosage according to the age, weight and all the other factors specific to the subject to be treated.

The following examples illustrate compositions according to the invention:

EXAMPLE A

Gelatine capsules in doses of 50 mg of active product having the following composition are prepared according to the usual technique:

| | |
|---|---|
| Active product | 50 mg |
| Cellulose | 18 mg |
| Lactose | 55 mg |
| Colloidal silica | 1 mg |
| Sodium carboxymethyl starch | 10 mg |
| Talc | 10 mg |
| Magnesium stearate | 1 mg |

EXAMPLE B

Tablets in doses of 50 mg of active product having the following composition are prepared according to the usual technique:

| | |
|---|---|
| Active product | 50 mg |
| Lactose | 104 mg |
| Cellulose | 40 mg |
| Polyvidone | 10 mg |
| Sodium carboxymethyl starch | 22 mg |
| Talc | 10 mg |
| Magnesium stearate | 2 mg |
| Colloidal silica | 2 mg |
| Hydroxymethylcellulose, glycerine, titanium oxide (72-3.5-24.5) qs 1 finished film-coated tablet containing | 245 mg |

EXAMPLE C

An injectable solution containing 50 mg of active product having the following composition is prepared:

| | |
|---|---|
| Active product | 50 mg |
| Benzoic acid | 80 mg |
| Benzyl alcohol | 0.06 ml |
| Sodium benzoate | 80 mg |
| Ethanol at 95% | 0.4 ml |
| Sodium hydroxide | 24 mg |
| Propylene glycol | 1.6 ml |
| Water | qs 4 ml |

What is claimed is:

1. A method for the treatment or prevention of diabetes or a complication of diabetes, comprising administering to a host in need of such treatment or prevention an effective amount of one or more compounds of formula (I);

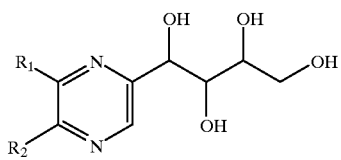
(I)

in which $R_1$ represents a hydrogen atom and $R_2$ represents a chain of formula:

$$—CH_2—CHOH—CHOH—CH_2OH \qquad (A)$$

or $$—CHOH—CHOH—CHOH—CH_2OH \qquad (B)$$

or $R_1$ represents a chain of formula (A) and $R_2$ represents a hydrogen atom.

2. A method for the treatment or prevention of diabetes or a complication of diabetes, comprising administering to a host in need of such treatment or prevention a pharmaceutical composition comprising one or more compounds of formula (I):

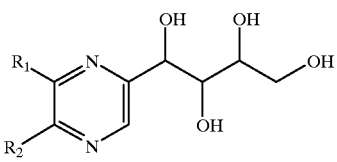
(I)

in which $R_1$ represents a hydrogen atom and $R_2$ represents a chain of formula:

$$—CH_2—CHOH—CHOH—CH_2OH \qquad (A)$$

or $$—CHOH—CHOH—CHOH—CH_2OH \qquad (B)$$

or $R_1$ represents a chain of formula (A) and $R_2$ represents a hydrogen atom, together with a pharmaceutically acceptable carrier.

* * * * *